US00PP16629P3

(12) United States Plant Patent
Moon

(10) Patent No.: US PP16,629 P3
(45) Date of Patent: Jun. 13, 2006

(54) TRIDENT MAPLE TREE NAMED 'ABMTF'

(50) Latin Name: *Acer buergerianum*
Varietal Denomination: ABMTF

(75) Inventor: Dwayne C. Moon, Walton County, GA (US)

(73) Assignee: Southern Selections, LLC, Loganville, GA (US)

( * ) Notice: Subject to any disclaimer, the term of this patent is extended or adjusted under 35 U.S.C. 154(b) by 34 days.

(21) Appl. No.: 10/900,653

(22) Filed: Jul. 28, 2004

(65) Prior Publication Data

US 2006/0026726 P1 Feb. 2, 2006

(51) Int. Cl.
*A01H 5/00* (2006.01)

(52) U.S. Cl. ..... Plt./224

(58) Field of Classification Search ..... Plt./224
See application file for complete search history.

(56) References Cited

U.S. PATENT DOCUMENTS

PP9,576 P 6/1996 Glenn

*Primary Examiner*—Anne Marie Grunberg
*Assistant Examiner*—June Hwu
(74) *Attorney, Agent, or Firm*—Polster, Lieder, Woodruff & Lucchesi L.C.

(57) ABSTRACT

A Trident maple tree (*Acer buergerianum*) named 'ABMTF' having an upright oval canopy, dense branching, smooth bark that has minimal exfoliation, and vigorous growth rate, and is capable of being reproduced reliably from vegetative cuttings.

7 Drawing Sheets

Latin name of genus and species: *Acer buergerianum.*
Variety denomination: Trident maple tree which I have named 'ABMTF'.

BACKGROUND OF THE INVENTION

Discovery

I discovered my new tree in a nursery production field of Trident maples purchased from a nursery in Florida that provided these trees as a randomly open-pollinated *Acer buergerianum* seedlings during the winter of 1995. This group of seedlings was grown in a liner field and then transplanted to an adjacent production field in Loganville, Walton County, Ga. during the winter of 1996. It was here that I discovered the claimed cultivator ABMTF.

Propagation

'ABMTF' was asexually propagated by the method of vegetative cutting at my direction in the summer of 2000 at Moon's Tree Farm in Loganville, Ga. Softwood cuttings three to five inches long were treated with 3000-ppm potassium indole-3-butyric acid (KIBA). The cuttings were then placed in peat pots filled with horticultural growing media and then intermittently misted for a period of five to six weeks. Currently our success rate for this method exceeds 90%.

Uniqueness

Seedling Trident maples are very diverse due to genetic variability in leaf size, branch structure, bark exfoliation and growth rate. My new tree was notably different from others in this seedling block due to its vigorous growth rate, dark green foliage, symmetrical branch structure, smooth, straight trunk and drought tolerance. These characteristics closely mimic the qualities found in larger maple species.

This invention has not been observed under all possible environmental conditions, but the progeny of 'ABMTF' have repeatedly shown that these characteristics are genetically stable.

Use

'ABMTF' has been observed for several years, and I believe it to be very useful for urban street plantings and commercial sites where a drought tolerant, medium-sized maple species is required. Nursery producers will also benefit from the increased growth rate and uniformity.

SUMMARY OF THE INVENTION

Background

*Acer buergerianum* is an oval-rounded to rounded small maple native to China. It performs well in the more acidic soils of zones 5 to 8 in the United States. It has been successfully grown from the mid-Atlantic area south to northern Florida and west to the eastern part of Texas and Oklahoma. I expect my new variety of Trident maple to perform as well as the species in these regions.

Industry Representation

Trident maple is typically seedling grown through random open-pollination. This method creates great variability of canopy height and width, branch structure, leaf color and size, and bark exfoliation. This genetic diversity has limited the landscape use of this tree due to a lack of uniformity. Presently, the only commercially available cultivar of this species of which I am aware is *Acer buergerianum* 'ABTIR' Streetwise, U.S. Plant Pat. No. 9,576. This cultivar has a growth rate greater than seedling grown trees, early exfoliation, and grayed-purple fall foliage.

My new variety differs from 'ABTIR' Streetwise, U.S. Plant Pat. No. 9,576 in the following characteristics, (1) a more rapid rate of growth, (2) different branch characteristics, and (3) bark smoothness. According to the description of 'ABTIR,' this tree reached a height of eighteen feet after eight years. My new variety 'ABMTF' grew from a twelve-inch seedling in the winter of 1995 to a height of twenty-one feet and a spread of thirteen feet when it was transplanted in November of 2000 (a period of 5 years). The angles of the primary and secondary branches are more distinct and the ends consistently roll upward. Finally, the bark of Streetwise is fluted and exfoliates at an early age whereas 'ABMTF' has a very smooth bark and has less exfoliation.

DESCRIPTION OF THE PHOTOGRAPHS

The accompanying photographs illustrate this new Trident variety with color as true as reasonably possible in this type of color photography.

DETAILED DESCRIPTION

Botanical Description of the Plant

Figure 1:
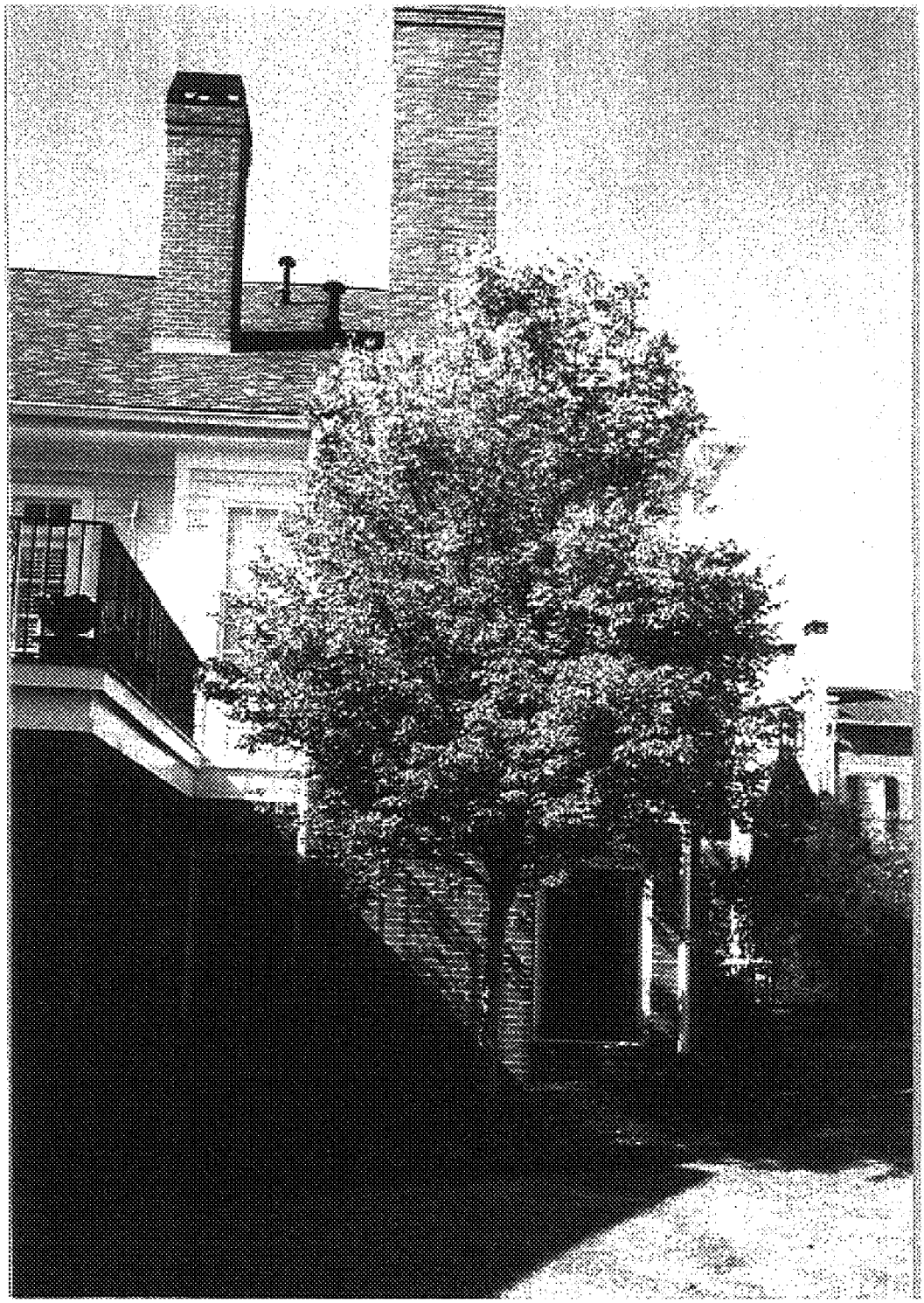
FIG. 1 is a photograph of the claimed cultivar taken in the summer of 2001 at an observation area showing form and habit. The tree is seven years old.
Figure 2:
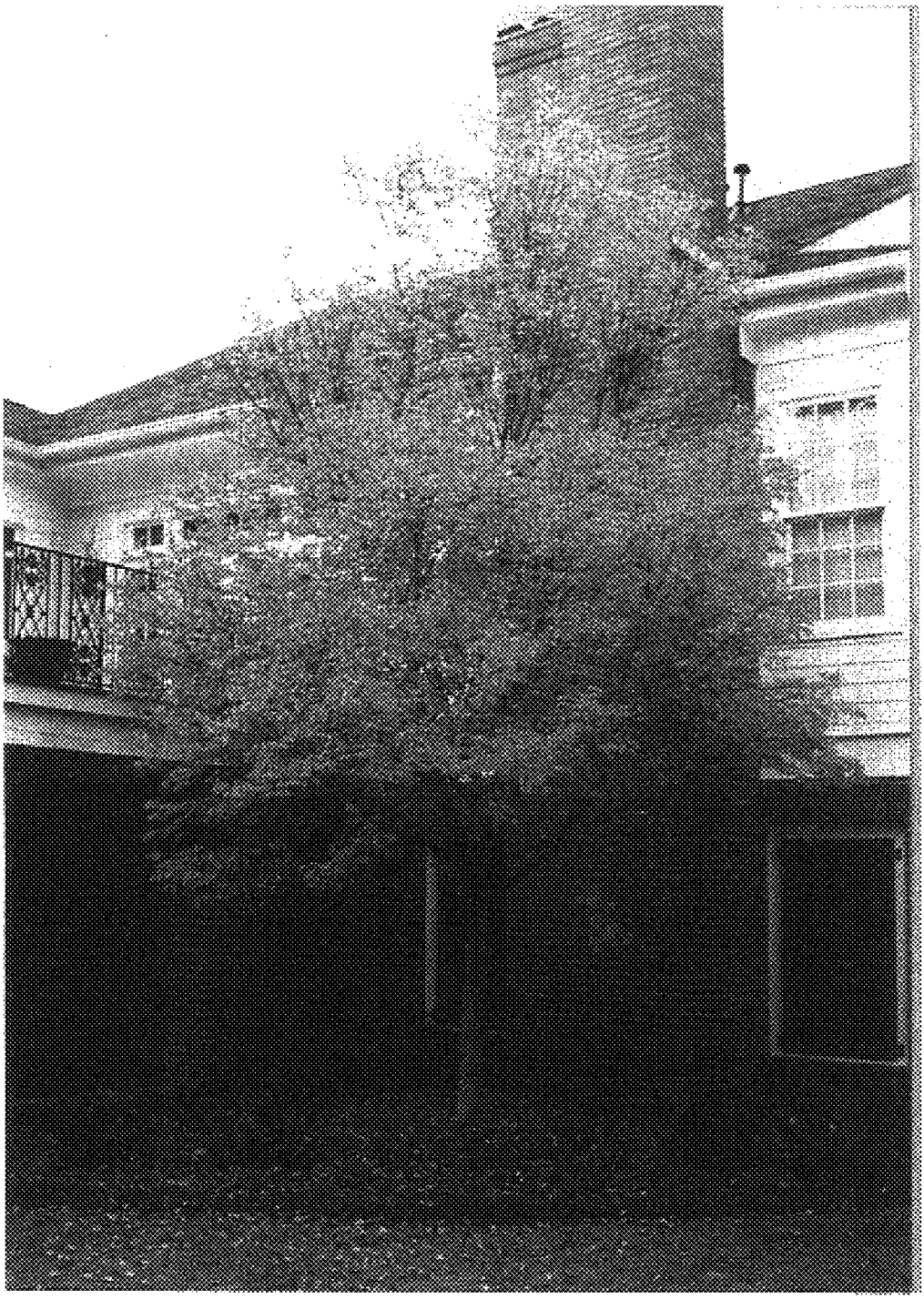
FIG. 2 is a photograph of the claimed cultivar taken in the fall of 2001 showing variations in fall color and branch structure. The tree is seven years old.
Figure 3:
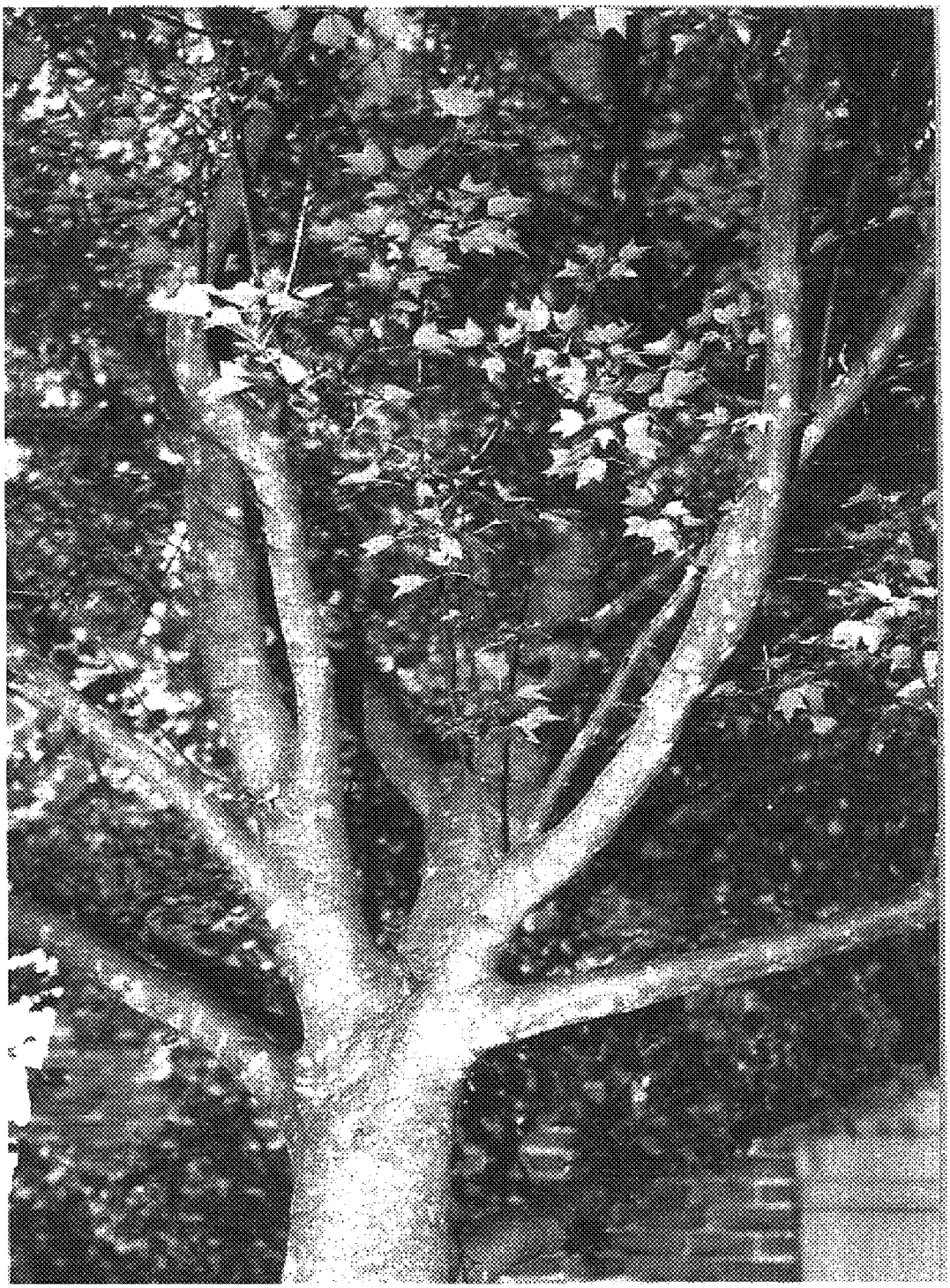
FIG. 3 is a photograph of the interior canopy of the claimed cultivar.
Figure 4:
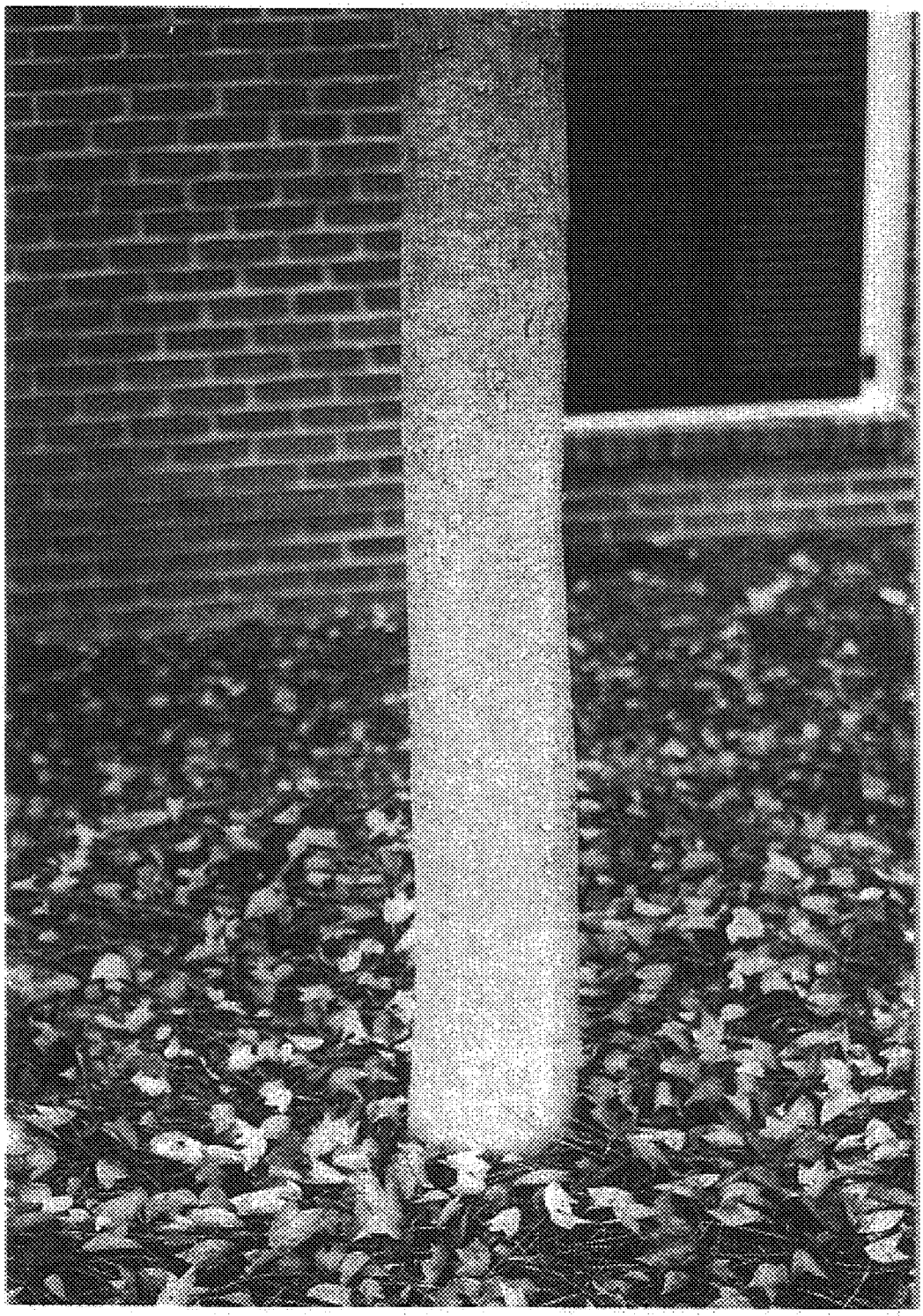
FIG. 4 is a photo of the bark of the claimed cultivar at six-inch caliper showing color, smoothness, and minimal exfoliation.
Figure 5:
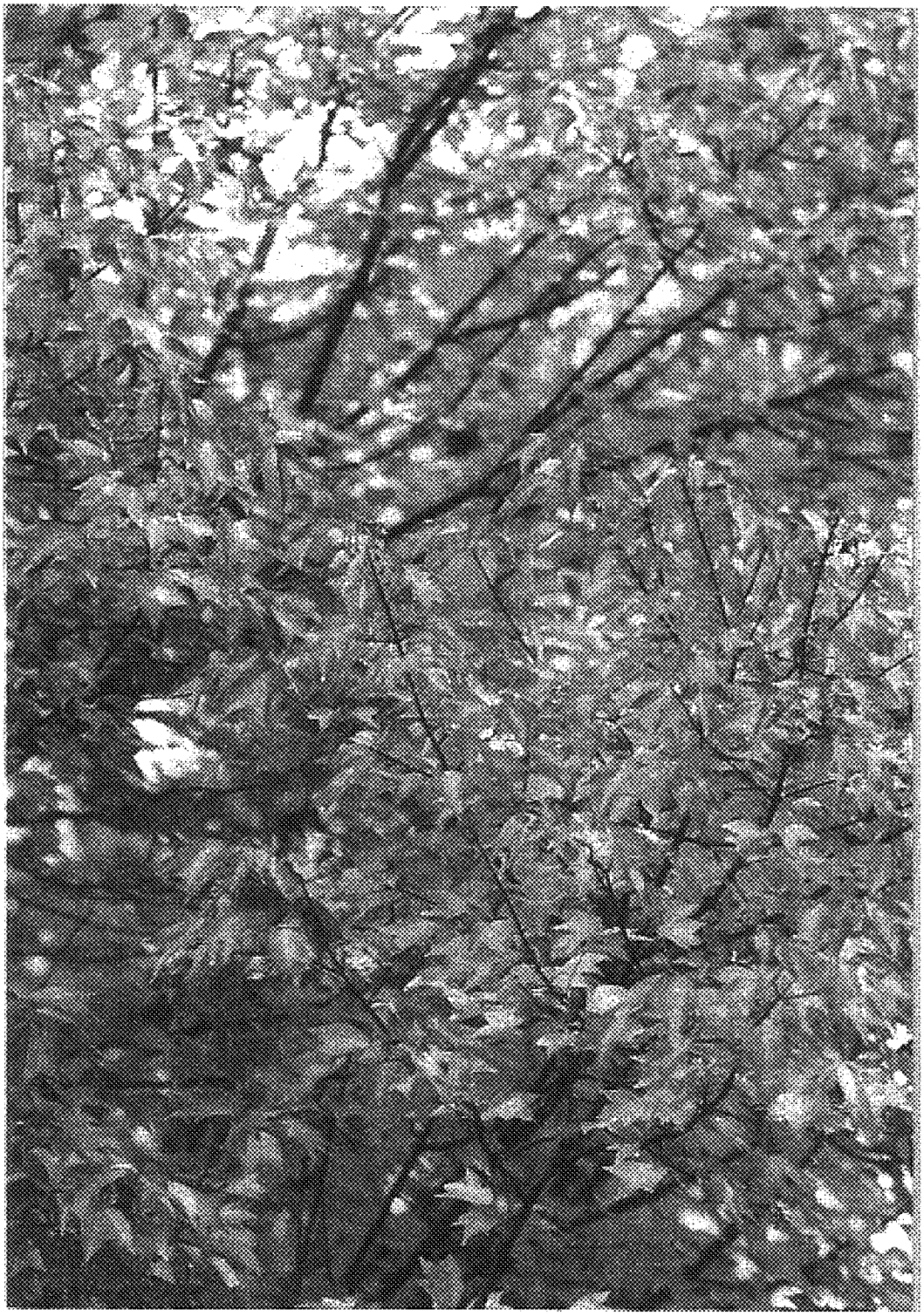
FIG. 5 is a photo close-up of fall foliage and variation of color.
Figure 6:
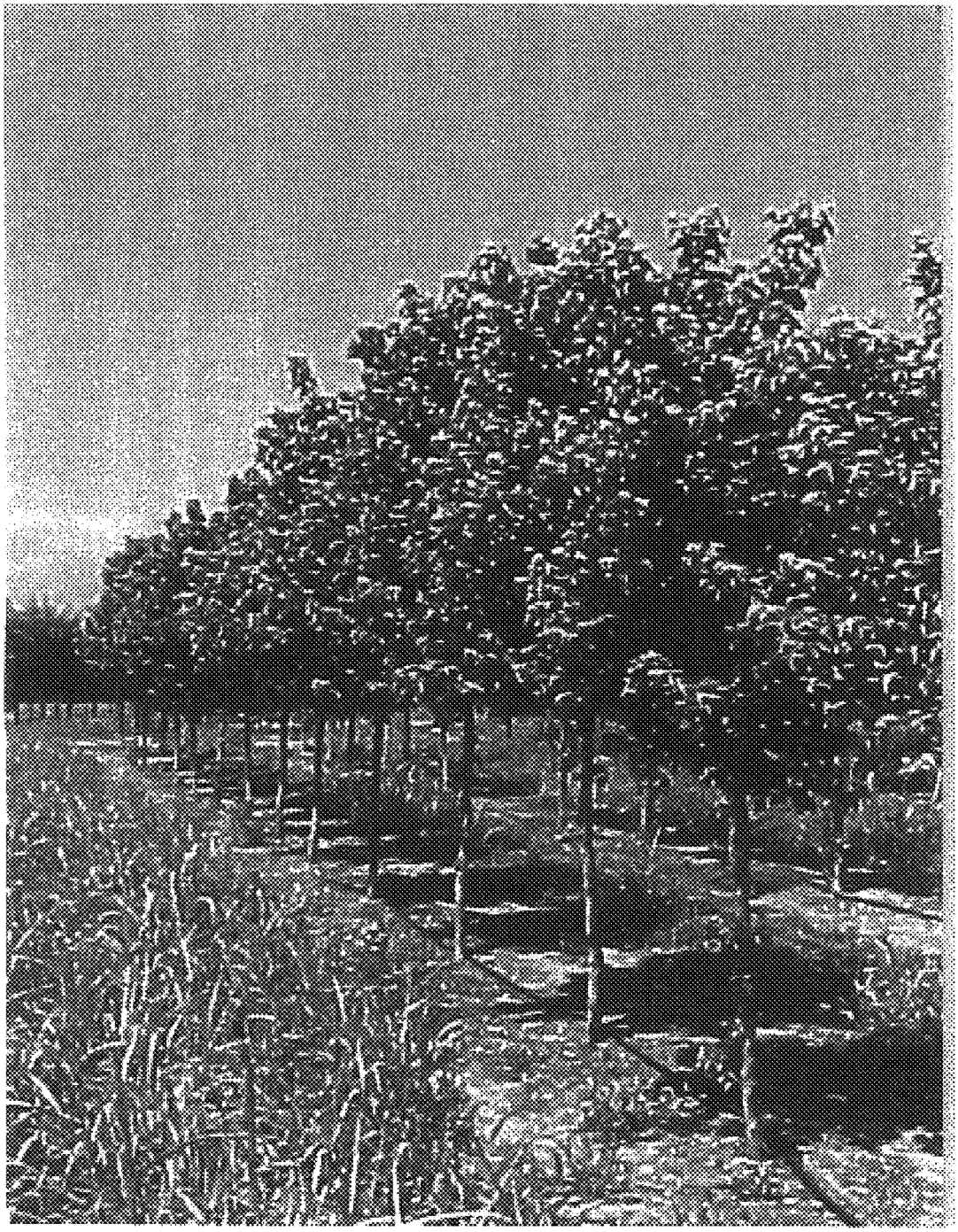
FIG. 6 is a field row shot of progeny at two-inch caliper.
Figure 7:
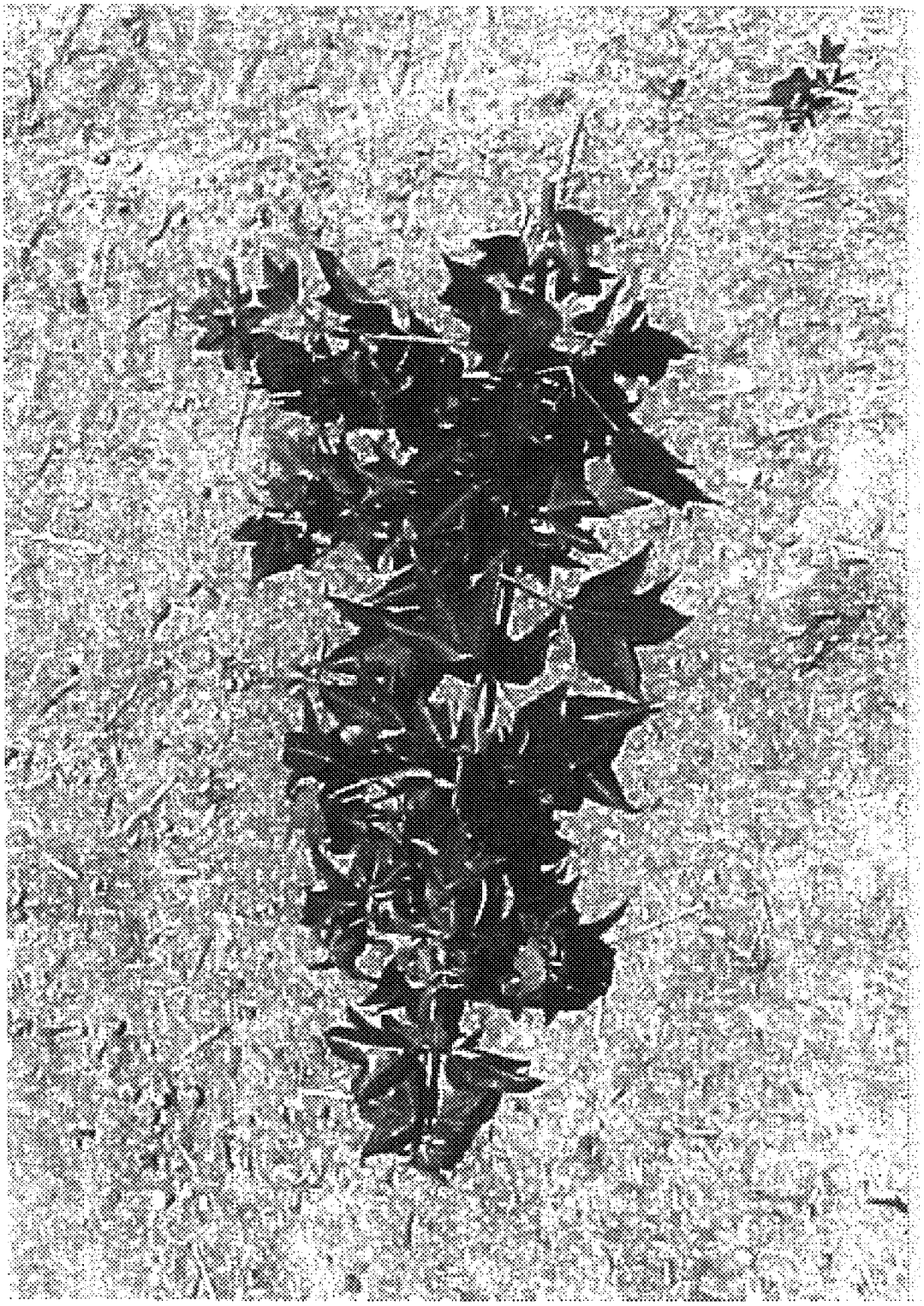
FIG. 7 is a photo of summer foliage showing leaf shape.

This invention has not been observed under all possible environmental conditions. The phenotype may vary with variations in growing environment, without, however, any variations in genotype. 'ABMTF' is currently being grown in fields adjacent to 6327 Hwy. 20, Loganville, Walton County, Ga. This particular area of Walton County has a clay loam soil type located in USDA Zone 7 and has an average rainfall of 30–60 inches annually. The following is a detailed description of 'ABMTF' Trident maple at age seven with color terminology in accordance with The Royal Horticulture Society (R.H.S.) Colour Chart, except where the context indicates a term having its ordinary dictionary meaning.

Parentage: Chance seedling random open-pollinated Trident maple parentage purchased from supplier in Florida.

Propagation: Genetically stable characteristics reproduced through asexual, vegetative softwood cuttings.

Locality where grown and observed: City of Loganville, County of Walton, State of Ga.

Size and growth rate: At time of transplant, the new tree was five years old and measured 5.5" caliper at 12 inches above the ground. The height was 21 feet and the width was 13 feet, thus providing a height to width ratio of 1.61. Prior to transplanting, the tree had an average growth rate of 1.25" caliper per year. This same rate of growth has been evident in the progeny.

Vigor: In field test on liner stock, my tree, 'ABMTF,' was grown next to 'ABTIR' and seedling material. With the same environmental conditions 'ABMTF' was 30% larger than the seedlings and 10% larger than 'ABTIR.'

*Tree shape*.—Upright oval with very dense foliage.

*Trunk*.—Smooth and unfluted with minimal exfoliation. Some stripe detail is evident which causes the coloring to vary between greyed-green (RHS 197A) and greyed-brown (RHS 199D).

Branching habit: More dense than species, primary lower branching emerges at about 10 to 15 degree angle with 20% of branch end curving upward. Branching toward the top third of the tree has 50 to 60 degree angles.

Branches: Hardwood branching has a greyed-green (RHS 197B) coloring while soft wood branching is yellow-green (146C). Wood is rigid but smooth, with small greyed-white lenticels.

Foliage: Mature leaves are semi-gloss tri-lobed with each lobe being triangular. Width between outer lobes averages two to three inches. Distance from base of leaf to middle lobe is also two to three inches. Margin of leaf in lobe section tends to be slightly serrate. The color of the leaf front is a dark green (RHS 139A) while the backside is a greyed-green (RHS 189A). As new growth emerges, the coloring is a greyed-red (RHS 178A). During the fall, foliage is varied between yellow-orange (RHS 20B) through a greyed-red of (RHS 179B). The petiole is a yellow-green (RHS 146C), measures about two inches and is smooth.

*Buds*.—Conical, reddish-brown (RHS 176C), ¼ inch long and pyramid.

*Stems*.—Slender, grayed-brown (RHS 199D) with pubescence.

*Flower*.—Small, greenish-yellow (RHS 145B) in slightly rounded clusters during mid-spring.

*Fruit*.—Yellowed-green (RHS 144C) double samaras ¾ inch to one inch long and ¼ inch wide, formed in autumn.

*Disease and pest*.—During the evaluation period, I have not seen disease or pest damage on the parent or the progeny.

*Hardiness*.—USDA hardiness zone 5–8.

I claim:

1. A new and distinct variety of Trident maple tree (*Acer buergerianum*) named 'ABMTF' substantially as illustrated and described herein.

* * * * *